(12) United States Patent
Peuker et al.

(10) Patent No.: US 7,854,721 B2
(45) Date of Patent: Dec. 21, 2010

(54) SYRINGE ASSEMBLY

(75) Inventors: Marc Peuker, Schondorf (DE); Arno Hohmann, Munich (DE); Michael Knee, Peiβenberg (DE)

(73) Assignee: 3M Espe AG, Seefeld (DE)

( * ) Notice: Subject to any disclaimer, the term of this patent is extended or adjusted under 35 U.S.C. 154(b) by 1062 days.

(21) Appl. No.: 10/928,485

(22) Filed: Aug. 27, 2004

(65) Prior Publication Data
US 2005/0119610 A1 Jun. 2, 2005

(30) Foreign Application Priority Data
Sep. 30, 2003 (EP) ................... 03022171

(51) Int. Cl.
*A61M 37/00* (2006.01)
*A61M 5/315* (2006.01)

(52) U.S. Cl. ........................................ 604/82; 604/231
(58) Field of Classification Search .................... 604/82, 604/219, 231
See application file for complete search history.

(56) References Cited

U.S. PATENT DOCUMENTS

| | | | |
|---|---|---|---|
| 1,624,990 A | 4/1927 | Smith | |
| 3,957,051 A | 5/1976 | Topham | |
| 5,817,055 A | 10/1998 | Ljungquist | |
| 5,891,087 A * | 4/1999 | Ohtani et al. | ................... 604/89 |
| 6,258,067 B1 | 7/2001 | Hill | |
| 2003/0040701 A1 | 2/2003 | Dalmose | |
| 2003/0097096 A1* | 5/2003 | Niedospial, Jr. | ............. 604/218 |

FOREIGN PATENT DOCUMENTS

| | | |
|---|---|---|
| FR | 592 193 | 7/1925 |
| GB | 2 066 376 | 8/1978 |
| LU | 88 699 | 8/1996 |
| WO | WO 98/01174 | 1/1998 |
| WO | WO 00/49319 | 8/2000 |

OTHER PUBLICATIONS

International Search Report dated May 26, 2004.

* cited by examiner

*Primary Examiner*—Nicholas D Lucchesi
*Assistant Examiner*—Victoria P Campbell

(57) ABSTRACT

The present invention relates to a syringe assembly comprising a syringe body member forming a syringe barrel having a syringe passageway passing through the length thereof; a discharge port being smaller in diameter than the syringe passageway and communicating with the syringe passageway at a front end thereof; at least one plunger member situated in the syringe barrel and dividing said syringe passageway into at least a first chamber at the front end of said syringe passageway and a second chamber at the back end of said syringe passageway, and comprising a plunger rod for actuating said plunger member; wherein said at least one plunger member being adapted for providing a flow connection between said chambers.

2 Claims, 4 Drawing Sheets

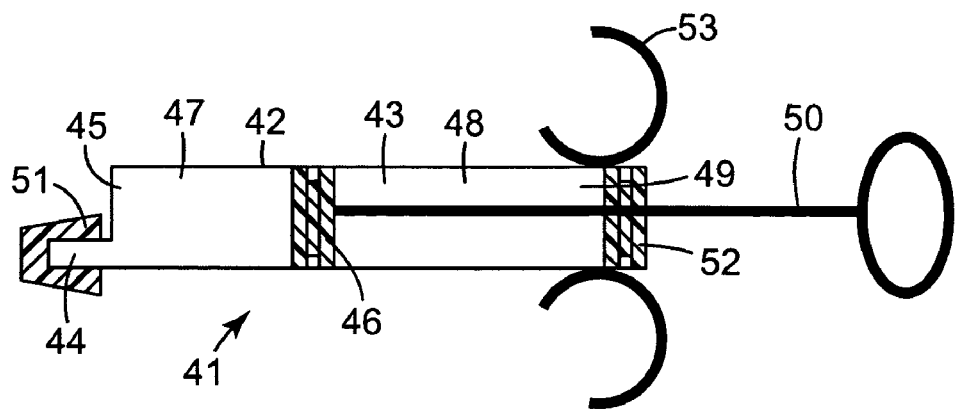
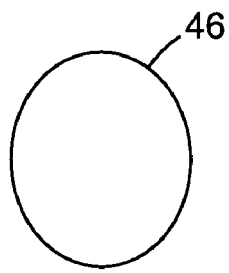 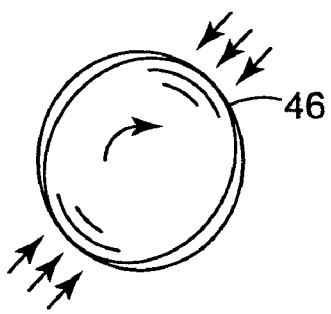
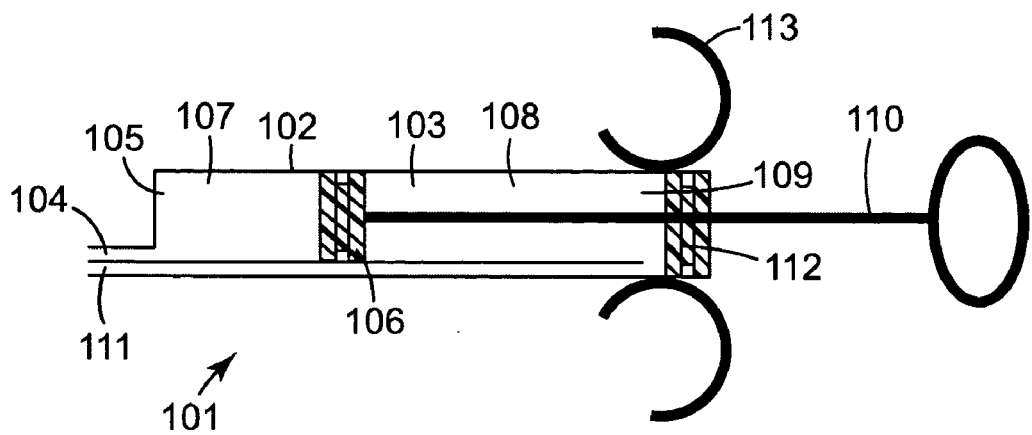

SYRINGE ASSEMBLY

This application claims priority from European Patent No. 03022171.7, filed Sep. 30, 2003.

FIELD OF THE INVENTION

The present invention relates to a syringe assembly, and in particular to a syringe assembly for medical and dental treatments and compositions.

BACKGROUND

Substances for medical or dental treatment are in many cases two- or multi-component compositions which have to be mixed prior to application. The components are stored separately from each other in order to avoid that they undergo an undesired reaction prior to application. For storage and subsequent mixing of the substances, appropriate packaging providing easy and cost effective handling is needed.

WO 00/49319 suggests an adaptor and system for enabling a material to be transferred from a first delivery means for delivering material to a second delivery means for delivering material and for enabling another material to be transferred from the second delivery means to the first delivery means.

However, conventional syringes for medical or dental treatment do not provide for separate storage of the different components of the substances and for mixing of substances prior to application of the substances.

Furthermore, conventional syringes are disadvantageous in that the consumption of the substance applied is relatively high. A common method is to utilize the flow energy of the substance by forcing it to flow through a needle or discharge port of relatively small inner diameter in order to achieve a high flow velocity. However, only a small amount of the discharged substance reaches the treated target surface, and a relatively high amount of the substance is lost, and, for example, flows into the mouth of the patient.

SUMMARY OF THE INVENTION

The object of the present invention is to provide a syringe assembly that provides storage of multi-component substances and easy mixing of the multi-component substance prior to its application.

It is another object of the present invention to provide a syringe assembly that reduces the loss of discharged material.

These objects are achieved with a syringe assembly according to the accompanying claims.

According to a first aspect of the present invention, a syringe assembly comprises a syringe body member forming a syringe barrel having a syringe passageway passing through the length thereof, a discharge port being smaller in diameter than the syringe passageway and communicating with the syringe passageway at a front end thereof, at least one plunger member situated in the syringe barrel and dividing said syringe passageway into at least a first chamber at the front end of said syringe passageway and a second chamber at the back end of said syringe passageway, and comprising a plunger rod for actuating said plunger member, said at least one plunger member being adapted for providing a flow connection between said chambers.

Preferably, said at least one plunger member comprises at least one flow passageway therethrough connecting said chambers. During movement of the plunger member, the volumes of the two chambers change in an opposite manner, thus providing a flow through the flow passageway. The components are mixed with each other. However, mixing is also possible without movement of the plunger member, it merely takes more time.

Preferably, said at least one plunger member is a valve-type plunger member being selectively openable or closeable, respectively. More preferably, said at least one plunger member is openable or closeable, respectively, by turning said plunger rod around its longitudinal axis. According to a preferred embodiment, said at least one plunger member comprises a first stationary part comprising at least one flow passageway, and a second displaceable part comprising at least one flow passageway, said first part and said second part being arranged adjacent to each other. In order to establish a flow connection between said two chambers, said flow passageways in said stationary and displaceable member are brought in-line with each other by displacing, preferably rotating, said displaceable member relative to the stationary member.

More preferably, said first part of said plunger member is adapted to provide an anti-twist function. Most preferably, said first part of said plunger member comprises an elliptical shape in order to provide such anti-twist function. Alternatively or in addition, said first part of said plunger member comprises one or more grooves being engagable with corresponding one or more webs provided at the inner surface of said syringe barrel. Alternatively or in addition, said first part of said plunger member frictionally engages the inner surface of said syringe barrel. Thus, the first part is held fixed while the second part can easily be twisted.

According to a further preferred embodiment, said at least one plunger member comprises at least two check-valve passages with flow passages in opposite directions. Thus, the components are forced to flow through different passages while moving the plunger back and forth.

Preferably, the assembly comprises a separator valve being located between said plunger member and the back end of said syringe passageway thus dividing said second chamber into two sub-chambers. More preferably, said separator valve is slidably engaged at said plunger rod. The separator valve will be moved back by movement of the plunger member into its final back position. During this procedure, the component contained in the sub-chamber adjacent to the plunger member flows over to the first chamber via the flow passage way in the plunger member. After the plunger member has reached the separator valve, the component in the other sub-chamber flows over into the first chamber via the flow passageways in the separator valve and the plunger member. Finally, the plunger member is moved back and forth thus mixing the three components (contained in the first chamber and the sub-chambers) homogenously together while the separator valve remains in the final back position.

It is preferred that said flow passageways comprises one or more mixing elements, preferably mixing helixes. This supports a homogenous mixing of the components. Alternatively, the mixing elements form the plunger member or part of it.

According to another preferred embodiment, said at least one plunger member is elastic and of non-circular cross-section.

Preferably, the assembly further comprises an entrance port to said syringe passageway being located adjacent to said discharge port.

With the present invention, it is possible to freely select the mixing ratio without any need to change the entire design/construction.

According to a second aspect of the present invention, a syringe assembly comprises a syringe body member forming a syringe barrel having a syringe passageway passing through the length thereof, a discharge port being smaller in diameter than the syringe passageway and communicating with the syringe passageway at a front end thereof, at least one plunger member situated in the syringe barrel and dividing said syringe passageway into at least a first chamber at the front end of said syringe passageway and a second chamber at the back end of said syringe passageway, and comprising a plunger rod for actuating said plunger member, and an entrance port to said syringe passageway being located adjacent to and separated from said discharge port.

It is preferred according to the first and second aspect of the present invention that said entrance port enters said syringe passageway at a back end thereof. In other words, a channel is provided extending from the tip of the syringe assembly to the back end portion of the syringe passageway. Preferably, movement of said plunger member causes dispensing of material contained in said first chamber through said discharge port and sucking of superfluous dispensed material back into said second chamber through said entrance port. Thus, a "double-action construction" is provided. Upon movement of the plunger, the volumes of the two chambers change in an opposite manner, thus providing both the dispensing and suction effect at the same time.

The assembly preferably further comprises a seal member located at the front end of said syringe passageway slidably accommodating the front end of said plunger rod, said plunger member being accommodated on said plunger rod so that it is movable between said front end seal member and a back end seal member of said syringe barrel. In this preferred embodiment, the plunger rod is led through both chambers. This can easily be achieved by extending the front end of the syringe barrel in order to create the required length for the movement of the plunger rod. The front end chamber is sealed against this extension by means of the seal member. The advantage of this specific construction is that it is possible to provide chambers having equal volumes.

Alternatively, the assembly comprises a front end plunger member and a back end plunger member being connected to said plunger rod, said front end plunger member dispensing material through said discharge port, and said back end plunger member sucking of superfluous dispensed material back into said syringe passageway. This arrangement provides three chambers in the syringe barrel, one chamber (the front end chamber) between the front end plunger member and the discharge port, a second chamber (the back end chamber) between the back end plunger member and the back end of the syringe barrel (for accommodating the sucked material), and, finally, a further chamber between the two plunger members. This further chamber is not used. Preferably, said syringe passageway comprises a stepped configuration along its longitudinal direction. With this stepped configuration, chambers having equal volumes can easily be provided. The two plunger members then have different diameters.

According to a third aspect of the present invention, a syringe assembly comprises a syringe body member forming a syringe barrel having a syringe passageway passing through the length thereof, a plunger member situated in the syringe barrel and dividing said syringe passageway into at least a first chamber at the front end of said syringe passageway and a second chamber at the back end of said syringe passageway, and comprising a plunger rod, a first channel being smaller in diameter than the syringe passageway and communicating with said back end chamber through said plunger member, a second channel to said front end chamber of said syringe passageway being located adjacent to and separated from said first channel, said first channel and said second channel being provided in a rod-like member connected to said plunger member and slidably accommodated at said front end of said syringe barrel.

In this third aspect of the present invention, the syringe assembly comprises a first channel and a second channel which essentially corresponds to the discharge port and the entrance port comprised in the syringe assemblies of the first and second aspect of the present invention. However, according to the third aspect of the present invention, the first and second channels function as discharge ports or entrance ports, depending on the direction of movement of the plunger member relative to the syringe barrel. Since the first channel communicates with the back end chamber, material is discharged through the first channel if the plunger member is moved towards the back end of the syringe assembly because due to this movement the volume of the back end chamber is reduced. During the same movement, the volume of the front end chamber is increasing so that superfluous discharged material is sucked back into the syringe barrel through the second channel, thus providing an entrance port. On the other hand, in case the plunger member is moved towards the front end of the syringe assembly, the volume of the front end chamber is reduced so that material is discharged through the second channel. At the same time, material is sucked back into the syringe barrel, i.e. into the back end chamber, through the first channel.

BRIEF DESCRIPTION OF THE DRAWINGS

In the accompanying drawings:

FIG. 4 is a cross-sectional view of a syringe assembly according to an alternative embodiment of the syringe assembly of the present invention;

FIGS. 5a and b show schematic top views of the plunger member of the syringe assembly according to FIG. 4;

FIG. 6 is a cross-sectional view of a syringe assembly according to a second aspect of the present invention;

DETAIL DESCRIPTION

With reference to FIGS. 1 through 5b, a syringe assembly according to a first aspect of the present invention with its different preferred embodiments will be described in the following.

Figure 1:
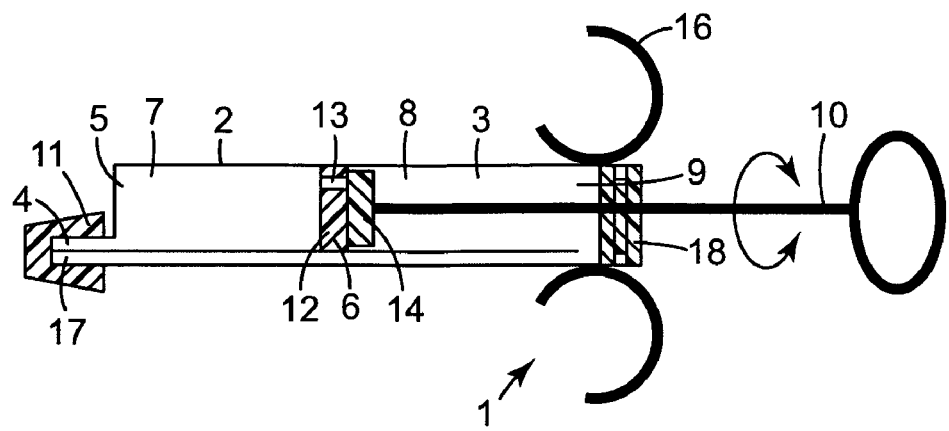
FIG. 1 is a cross-sectional view of syringe assembly according to a preferred embodiment of the first aspect of the present invention.

The syringe assembly 1 according to the first aspect of the present invention as shown in FIG. 1 comprises a syringe body member 2 that preferably has a tubular form with circular or elliptical cross-section. The syringe body member 2 forms a syringe barrel having a syringe passageway 3 passing through the length thereof. On the left side of the syringe body member 2 a discharge port 4 is shown for discharging material from the interior of the syringe assembly. The discharge port 4 is smaller in diameter than the syringe passageway 3, and communicates with the syringe passageway 3 at a front end 5 thereof. The discharge port 4 is preferably closed by a corresponding closure cap 11. In the preferred embodiment shown in FIG. 1, syringe assembly 1 further comprises an entrance port 17. The function and details of the entrance port will be described below.

In the interior of the syringe body member 2, a plunger member 6 is present that divides the syringe passageway 3 into at least a first chamber 7 at the front end 5 of the syringe passageway 3 and a second chamber 8 at the back end 9 of the syringe passageway 3. The plunger member 6 comprises a plunger rod 10 that extends from the plunger member 6 through a back end seal 18 to the exterior of the syringe body member 2. The plunger rod 10 can be used for actuating the plunger member. According to the first aspect of the present invention, the at least one plunger member 6 is adapted for providing a flow connection between the front end chamber and the back end chamber 8. Additional handles 16 are preferably provided. Back end seal 18 contains a fluid-proof lead through for accommodating plunger rod 10.

In order to provide such a flow connection between the two chambers, the plunger member 6 preferably comprises at least one flow passageway 13 therethrough that connects these two chambers. The plunger member 6 shown in FIG. 1 is a valve-type plunger member that is selectively openable or closeable, respectively. In particular, the valve-type plunger member 6 is openable or closeable, respectively, by turning the plunger rod 10 around its longitudinal axis.

Figure 2A:
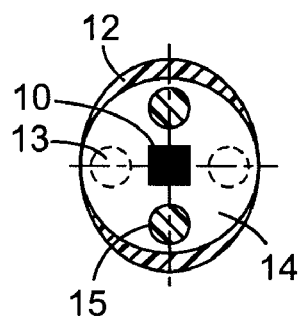
FIGS. 2A, 2B and 2C are top views of the plunger member of the syringe assembly shown in FIG. 1, FIG. 2A showing the plunger member in its closed position, FIG. 2B showing the plunger member being activated, and FIG. 2C showing the plunger member in its opened position.
Figure 2B:
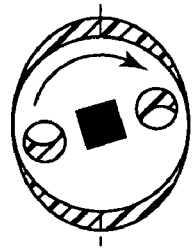
Figure 2C:
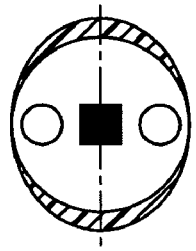

FIGS. 2A, B and C show the plunger member 6 in more detail, FIG. 2A shows the plunger member in a position where the valve is closed. FIG. 2B shows the activation of the plunger member 6. Finally, FIG. 2C shows the plunger member 6 at a position where the valve is open. The plunger member 6 is comprised of two components, that are displaceable with respect to each other, for example a first stationary part 12 that comprises at least one flow passageway 13, and a second displaceable part 14, also comprising at least one flow passageway 15. The first part and the second part are arranged adjacent to each other, as is clearly shown in FIGS. 1 and 2A-C. The second displaceable part 14 is connected to the plunger rod 10. As shown in, FIG. 2A, in its closed position, the displaceable part 14 of the plunger member 6 is located with respect to the first part 12 such that the flow passageway 13 and the flow passageway 15 are not in line with each other, the second displaceable part 14 closes the flow passageway 13 in the first stationary part 12. However, upon activation of the second displaceable part 14 by means of the plunger rod 10, the flow passageways 13 and 15 are brought in line with each other, as shown in FIG. 2C. In the specific embodiment shown in FIGS. 2A-C, two flow passageways 13 and 15 are provided so that there are finally two passageways in the plunger member 6.

Preferably, the first stationary part 12 of the plunger member 6 is adapted to provide an anti-twist function in order to guarantee that only the displaceable part 14 is displaceable and that the stationary part 12 remains stationary so that the front end chamber 7 is tightly sealed against the back end chamber 8. Such an anti-twist function is preferably provided by means of a plunger member comprising an elliptical shape. Due to such an elliptical shape, the stationary part 12 cannot be rotated within the syringe body member 2 (also comprising an elliptical shape). Alternatively, or in addition, the plunger member comprises one or more grooves around its circumference which are engageable with one or more corresponding webs provided at the inner surface of the syringe barrel. Such an engagement of grooves and webs prevents a displacement or rotation of the stationary part 12. Alternatively, or also in addition, the plunger member 6 frictionally engages the inner surface of the syringe barrel. This feature may help to provide an anti-twist function in case the syringe barrel and the plunger member have a circular cross-section.

According to an alternative embodiment of the first aspect of the present invention, the at least one plunger member 6 does not comprise two different parts but just a single part with at least two check-valve passages with flow passages in opposite directions. Such check-valves force the components contained in the different chambers to flow through different passages while the plunger member is moved back and forth.

Figure 3:
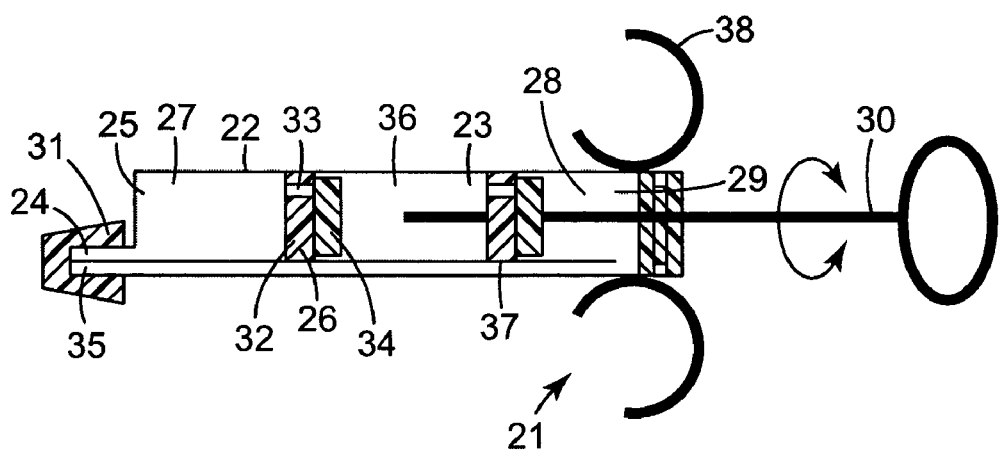
FIG. 3 is a cross-sectional view of a syringe assembly according to further preferred embodiment of the present invention.

FIG. 3 shows an alternative embodiment of the syringe assembly according to the first aspect of the present invention. Syringe assembly 21 shown in FIG. 3 comprises a syringe body member 22 forming a syringe barrel having a syringe passage 23 passing through the length thereof. A discharge port 24 (that is preferably closed by a closure cap 31) has a smaller diameter than the syringe passageway 23 and communicates with the syringe passageway 23 at front end 25 of the syringe assembly 21. In the interior of the syringe assembly, at least one plunger member 26 is provided. In the shown embodiment, the plunger member 26 consists of two parts, i.e. first (stationary) part 32 with flow passageway 33, and second displaceable part 34. The displaceable part 34 is connected to connecting rod 30. In addition, a separator valve 37 is provided in the syringe body member 22. Separator valve 37 is slideably engaged at the plunger rod 30. Due to the arrangement with plunger member 26 and separator valve 37, a first chamber 27 at front end 25 is provided. Furthermore, a second chamber is divided by the separator valve into two sub-chambers 28 and 36. Sub-chamber 28 is located at the back end 29 of the syringe assembly, and sub-chamber 36 is between first chamber 27 and sub-chamber 28. The separator valve 37 will be moved back to the back end 29 by movement of the plunger member 26 into its final back position. During this procedure, the component contained in sub-chamber 36 flows over to the first chamber 27 via the passageway in plunger member 26. After the plunger member 26 has reached the separator valve 37, the component contained in sub-chamber 28 flows over into the first chamber 27 via the passageways in the separator valve and the plunger member. Finally, the plunger member 26 is moved back and forth thus mixing the three components homogeneously together while the separator valve 37 remains in the final back position.

FIG. 3 also shows as a preferred feature entrance port 39 at the front end 25 of the syringe assembly 21. Furthermore, FIG. 3 shows preferred handles 38.

According to a further preferred embodiment of the first aspect of the present invention, as shown in FIG. 4, the syringe assembly 41 comprises an elastic plunger member 46 that divides the syringe body member 42 into a front end chamber 47 provided at front end 45 and a back end chamber 48 adjacent to back end 49. Plunger member 46 is connected to plunger rod 50 that extends from plunger member 46 through the syringe passageway 43, and through back end seal 52 to the exterior of the syringe assembly 41. Moving the plunger member 46 towards front end 45 causes the material contained in the syringe body member 42 to be discharged through discharge port 44. Discharge port 44 is preferably closed by closure cap 51. In the embodiment shown FIG. 4, the elastic plunger member 46 has an elliptical cross-section, as also shown in FIGS. 5a and 5b. In this embodiment, mixing of two different components contained in front end chamber 47 and back end chamber 48 is possible due to the elastic properties of the plunger member 46. A shown in FIG. 5b, displacement/rotation of the plunger member 46 by means of plunger rod 50 causes a compression of the plunger member 46 so that at those areas where the plunger member is compressed, flow channels are established that connect the front end chamber 47 and the back end chamber 48.

Turning now to FIG. 6, a second aspect of the present invention will be described. FIG. 6 shows a syringe assembly 101 that also comprises a syringe body member 102, syringe passageway 103 front end chamber 107 at front end 105, back end chamber 108 at back end 109, plunger member 106 connected to plunger rod 110, and a discharge port 104 at the front end 105 of the syringe assembly 101. In addition, the syringe assembly 101 of the second aspect of the present invention comprises an entrance port 111 at the front end of the syringe assembly 101. The entrance port 111 provides entrance to the syringe passageway 103, and is located adjacent to the end but separated from discharge port 104. As shown in FIG. 6, the entrance port preferably enters the syringe passageway 103 at a back end thereof, i.e. adjacent to back end seal 112. Thus, the entrance port in fact provides a channel extending from the front end 105 of the syringe assembly 101 to the back end 109. Plunger member 106 is moveable within the syringe body member 102 of the syringe assembly 101, and movement of the plunger member 106 causes dispensing of material contained in the first chamber 107 through the discharge board 104 and simultaneous sucking of superfluous dispensed material back into the second chamber 108. Thus, at the same time material is dispensed from the syringe assembly 101, superfluous material can be sucked back into the syringe assembly 101.

Figure 7A:
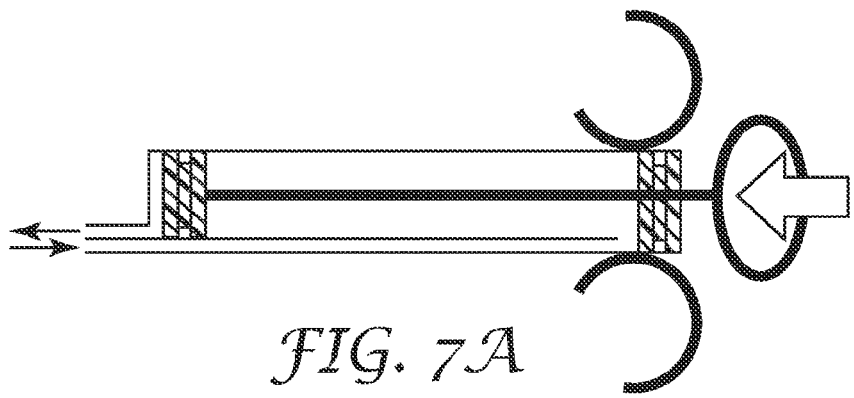
FIGS. 7a and b are cross-sectional views of the syringe assembly of FIG. 6 showing the plunger member in its front end final position (FIG. 7a) and in its back end final position (FIG. 7b)
Figure 7B:
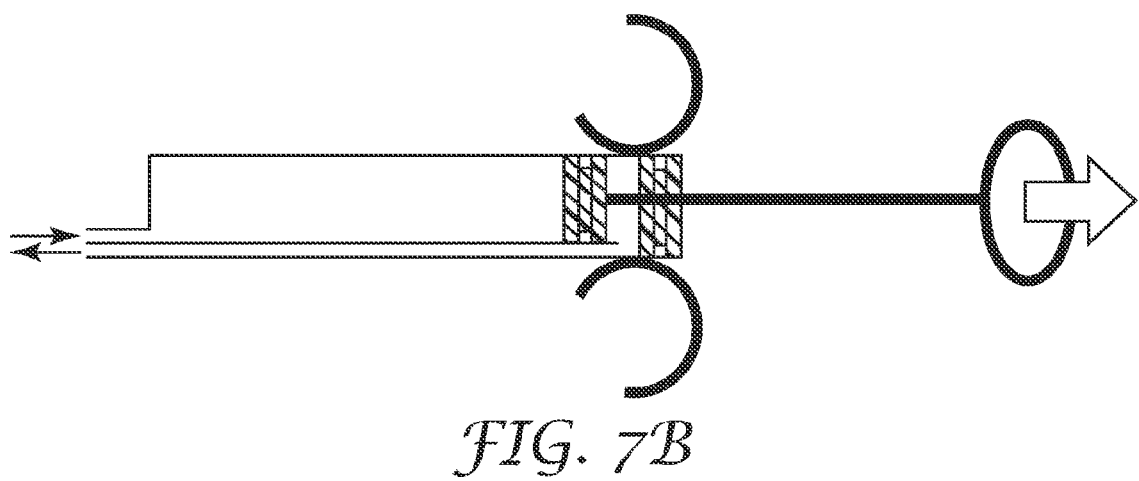

FIGS. 7a and 7b show the syringe assembly 101 according to the second aspect of the present invention in two different positions, i.e. with the plunger member 106 in its front end final position (FIG. 7a) and in its approximate back end final position (see FIG. 7b).

Figure 8:
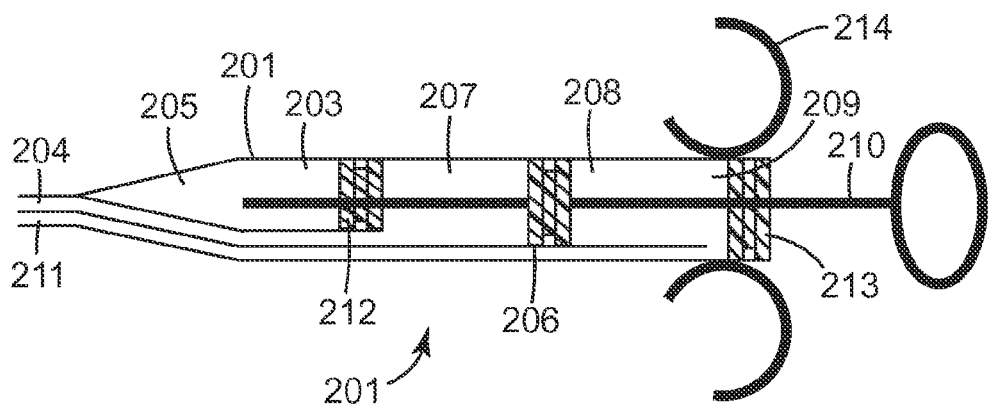
FIG. 8 is a cross-sectional view of a syringe assembly according to a preferred embodiment of the syringe assembly according to the second aspect of the present invention.

FIG. 8 shows an alternative embodiment of the second aspect of the present invention. In addition to plunger member 206 provided in the syringe body member 202 of syringe assembly 201, a front end seal 212 is present in this embodiment. Front end seal 212 is preferably identical to back end seal 213. Plunger member 206 divides syringe passageway 203 into a front end chamber 207 and a back end chamber 208. Front end chamber 207 is provided between front seal 212 and plunger member 206, and back end chamber 208 is provided between plunger member 206 and back end seal 213.

Plunger rod 210 is connected to plunger member 206, and is further slideably accommodated in front end seal 212 so that the plunger member 206 is moveable between the front end seal member 212 and the back end seal member 213 of the syringe assembly 201. This arrangement guarantees that the front end chamber 207 and the back end chamber 208 have essentially equal volumes. Material contained in front end chamber 207 can be dispensed through discharge port 204, and superfluous dispensed material can be sucked back into back end chamber 208 by means of entrance port 211.

Figure 9:
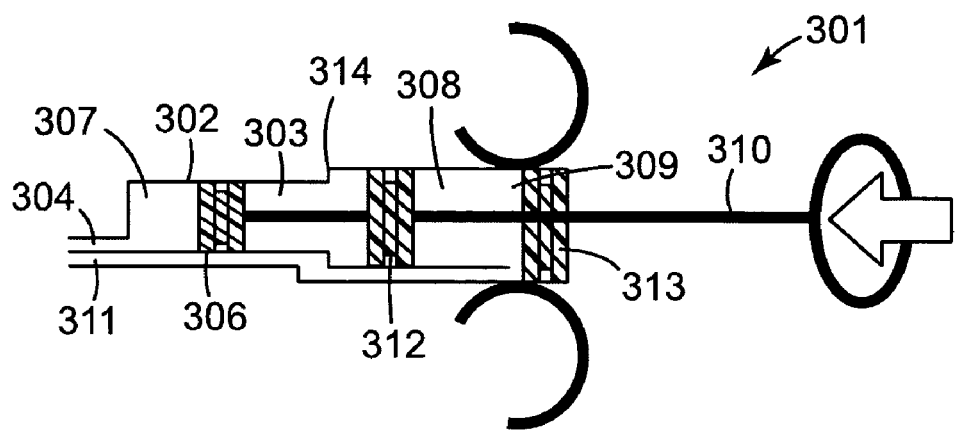
FIG. 9 is a cross-sectional view of a syringe assembly according to an alternative assembly of the second aspect of the present invention.

An alternative embodiment of the second aspect of the present invention is shown in FIG. 9. In this preferred embodiment, syringe body member 302 of syringe assembly 301 comprises a stepped configuration. The step is denoted by reference numeral 314. Syringe assembly 301 of this preferred embodiment comprises a front end plunger member 306 and a back end plunger member 312 that effectively provide three chambers within the syringe passageway 303. Front end chamber 307 is provided at front end 305 of syringe assembly 301, i.e. adjacent to discharge portion 304. Back end chamber 308 is provided between back end plunger 312 and back end closure seal 313. Furthermore, there is an additional chamber between the two plunger members that is not used, i.e. there is no material contained in this intermediate chamber.

Plunger rod 310 is connected to the front end plunger member 306 and the back end plunger member 312, and movement of the plunger rod 310 causes that material is discharged through discharge port 304, and superfluous material is sucked back into back end chamber 308 through entrance port 311.

Due to the stepped configuration, the front end plunger member 306 has a diameter that is smaller than the diameter of back end plunger member 312. Due to the stepped configuration, it is possible to provide a front end chamber 307 and a back end chamber 308 that have substantially equal volumes. Although the diameter of the back end chamber 308 is larger than the diameter of front end chamber 307, the volumes are substantially equal because the back end chamber 308 additionally accommodates a part of the plunger rod 310.

Figure 10:
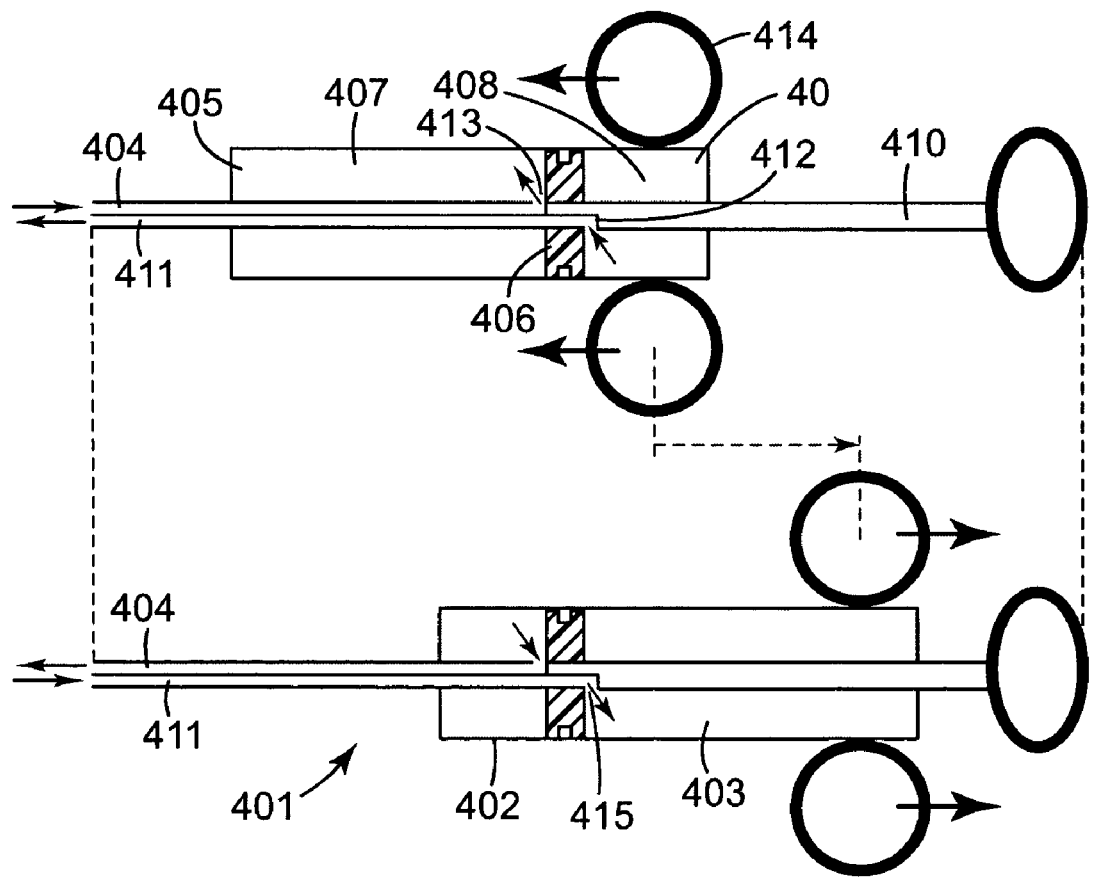
FIG. 10 shows two cross-sectional views of a syringe assembly according to a third aspect of the present invention, both cross-sectional views showing the plunger member in different positions.

FIG. 10 shows a syringe assembly 401 according to a third aspect of the present invention. Syringe assembly 401 comprises a syringe body member 402 providing a syringe passageway 403. A plunger member 406 divides the syringe passageway 403 into front end chamber 407 at front end 405, and back end chamber 408 at back end 409. Furthermore, plunger rod 410 is connected to plunger member 406.

The syringe assembly 401 according to this aspect of the present invention comprises a first channel 410 and a second channel 411. The second channel 411 is connected to the plunger member 406 such that it extends through the plunger member 406 and is open to back end chamber 408. In the shown embodiment, plunger rod 410 for this reason has a stepped configuration 412 adjacent to plunger member 406. Thus, through the second channel 411, a flow communication between back end chamber 408 an the exterior of the syringe assembly 401 is possible. First channel 404 is provided adjacent to second channel 411 but is shorter so that it opens into front end chamber 407. The upper drawing of FIG. 10 clearly shows the opening 413 left to plunger member 406. Through this opening 413, a flow communication between the front end chamber 407 an the exterior of the syringe assembly 401 is provided.

Preferably, the first channel and the second channel have a tubular configuration, and are provided both in a rod-like member.

Due to the specific configuration and length of the first and second channels, each of the first and second channels 404, 411 function as discharge port and entrance port, depending on the direction of movement of the plunger member. In case the plunger member 406 is moved by means of the plunger rod 410 towards the back end 409 (i.e. the two circular handle elements 414 are moved leftwards with respect to the plunger member 406, as denoted by the two arrows in the upper drawing of FIG. 10), the volume of back end chamber 408 is reduced so that material contained in back end chamber 409 is discharged through opening 415 and second channel 411. At the same time, the volume of front end chamber 407 is increased, and superfluous material is sucked back into the front end chamber 407 through the first channel 404.

The reverse operation is shown in the lower drawing of FIG. 10. Here, the plunger member 406 is moved towards the front end 405 of the syringe assembly 401, thus reducing the volume of front end chamber 407; material is thus discharged through the first channel 404, as indicated by the arrow facing leftwards. Furthermore, due to the increase in volume of back end chamber 408, superfluous material is sucked back through second channel 411.

The invention claimed is:

1. A syringe assembly comprising a syringe body member forming a syringe barrel having a syringe passageway passing through the length thereof;

a discharge port being smaller in diameter than the syringe passageway and communicating with the syringe passageway at a front end thereof;

at least one elastic plunger member having a non-circular cross-section situated in the syringe barrel and dividing said syringe passageway into at least a first chamber at the front end of said syringe passageway and a second chamber at the back end of said syringe passageway, and a plunger rod for actuating said plunger member;

said at least one plunger member being adapted for being rotated by turning the plunger rod around its longitudinal axis to cause compression of the plunger member, whereby the plunger member establishes a flow connection between said chambers due to the compression of the plunger member.

2. The assembly of claim 1, wherein the at least one plunger member comprises an elliptical cross-section.

* * * * *

UNITED STATES PATENT AND TRADEMARK OFFICE
CERTIFICATE OF CORRECTION

PATENT NO. : 7,854,721 B2  
APPLICATION NO. : 10/928485  
DATED : December 21, 2010  
INVENTOR(S) : Marc Peuker Page 1 of 1

It is certified that error appears in the above-identified patent and that said Letters Patent is hereby corrected as shown below:

Title Page, item (75)

Column 1 (Inventors); Line 3, delete "Peiβenberg" and insert -- Peißenberg --, therefor.

Column 5

Line 45; delete "detail," and insert -- detail. --, therefor.
Line 56; delete "in," and insert -- in --, therefor.
Line 59; After "other," insert -- i.e. --.

Column 7

Line 22; Delete "103" and insert -- 103, --, therefor.

Column 10

Line 8; Claim 1, after "passageway," insert -- wherein the second chamber is closed by a seal at the back end thereof, --.

Signed and Sealed this  
Third Day of January, 2012

David J. Kappos  
*Director of the United States Patent and Trademark Office*